United States Patent [19]

Deaton

[11] Patent Number: 5,252,455
[45] Date of Patent: Oct. 12, 1993

[54] PHOTOGRAPHIC SILVER HALIDE MATERIAL COMPRISING GOLD (I) COMPLEXES COMPRISING SULFUR- AND/OR SELENIUM-SUBSTITUTED MACROCYCLIC POLYETHER LIGANDS

[75] Inventor: Joseph C. Deaton, Rochester, N.Y.

[73] Assignee: Eastman Kodak Company, Rochester, N.Y.

[21] Appl. No.: 845,897

[22] Filed: Mar. 4, 1992

[51] Int. Cl.$^5$ .............................................. G03C 1/06
[52] U.S. Cl. ................................... 430/605; 430/603; 430/600; 430/612; 430/614; 430/607
[58] Field of Search ............. 430/605, 603, 600, 612, 430/614, 607

[56] References Cited

U.S. PATENT DOCUMENTS

| | | | |
|---|---|---|---|
| 3,046,132 | 7/1962 | Minsk | 430/605 |
| 3,046,134 | 7/1962 | Dann et al. | 430/603 |
| 3,046,135 | 7/1962 | Beavers | 430/605 |
| 3,062,646 | 11/1962 | Dann et al. | 430/446 |
| 3,271,157 | 9/1966 | McBride | 430/604 |
| 3,507,657 | 4/1970 | Kitze | 430/600 |
| 3,531,289 | 9/1970 | Wood | 430/604 |
| 4,752,560 | 6/1988 | Benard et al. | 430/523 |
| 4,782,013 | 11/1988 | Herz et al. | 430/564 |
| 4,865,965 | 9/1989 | Friour et al. | 430/569 |
| 5,049,484 | 9/1991 | Deaton | 430/605 |
| 5,049,485 | 9/1991 | Deaton | 430/605 |

FOREIGN PATENT DOCUMENTS

| | | |
|---|---|---|
| 246853 | 6/1987 | Fed. Rep. of Germany . |
| 249106 | 8/1987 | Fed. Rep. of Germany . |
| 57-074738 | 11/1982 | Japan . |
| 60-080840 | 5/1985 | Japan . |
| 2212641 | 9/1987 | Japan . |
| 63-259653 | 10/1988 | Japan . |
| 60-261252 | 10/1988 | Japan . |
| 63-292126 | 11/1988 | Japan . |
| 63-301939 | 12/1988 | Japan . |
| 3-037641 | 2/1991 | Japan . |
| 1038919 | 8/1983 | U.S.S.R. . |

OTHER PUBLICATIONS

Dvorkin, et al., *Chemical Abstracts*, vol. 113, No. 142680x, 1990, "Structure of $\mu$-1,10-dithia-4,7,13,16-tetraoxacyclooctadecanedichlorodiaurate(I)".

Dvorkin, A. A., Inst. Prikl. Fiz., Kishinev, USSR Dokl. Akad. Nauk SSSR, 1990, 311(5), pp. 1126–1129.

Huheey, J. E., *Inorganic Chemistry*, 2nd edition, 1978, pp. 481–482.

*Primary Examiner*—Charles L. Bowers, Jr.
*Assistant Examiner*—Geraldine Letscher
*Attorney, Agent, or Firm*—Paul A. Leipold

[57] ABSTRACT

This invention provides gold(I) complexes comprising sulfur- and selenium-substituted macrocyclic polyether ligands, photographic elements containing the compounds, and emulsions containing the compounds. The compounds include monomers and dimers having the following formulas, respectively:

$$[AuL]^+X^- \text{ or } [AuL]_2^{2+}2X^-$$

wherein $X^-$ is any suitable anion such as tetrafluoroborate, nitrate, etc., and wherein L is a macrocyclic ligand containing at least two thioether and/or selenoether linkages and comprising from about 12 to about 30 members in the ring. The general structural formula for the macrocyclic compounds L may be represented as follows:

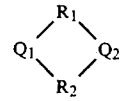

wherein $Q_1$ and $Q_2$ are each independently sulfur or selenium, and $R_1$ and $R_2$ are alkylene groups, the chain of which comprises from about 5 to 14 members that may include heteroatoms such as oxygen, sulfur, selenium, nitrogen, and that may include functional groups such as carboxylic ester or carboxylic amide linkages and the like. The alkylene group may be further substituted with alkyl groups or other functional groups such as carboxylic acids or esters, alcohols, and the like.

17 Claims, No Drawings

PHOTOGRAPHIC SILVER HALIDE MATERIAL COMPRISING GOLD (I) COMPLEXES COMPRISING SULFUR- AND/OR SELENIUM-SUBSTITUTED MACROCYCLIC POLYETHER LIGANDS

TECHNICAL FIELD

This invention relates to new gold(I) compounds comprising macrocyclic thioether or selenoether ligands and to photographic silver halide materials chemically sensitized with such gold(I) compounds.

BACKGROUND ART

Photographic silver halide materials are often chemically sensitized with one or more compounds containing labile atoms of gold, sulfur or selenium and the like to provide increased sensitivity to light and other sensitometric properties. Examples of typical chemically sensitized photographic silver halide emulsions are described in, for example, *Research Disclosure*, Item No. 308119, December 1989, Section III, and the references listed therein (Research Disclosure is published by Kenneth Mason Publications Ltd., Dudley Annex, 12a North Street, Emsworth, Hampshire PO 10 7DQ, England.)

Gold compounds may contain gold in the (I) or (III) oxidation state. However, those in the (I) oxidation state are preferred because those gold compounds in the (III) oxidation state may undergo side reactions that, for example, oxidize gelatin or other components in photographic emulsions. Among gold(I) compounds, trisodium aurous dithiosulfate is commonly known as a chemical sensitizer, but is not universally applicable because of the disadvantages this compound provides. In particular, this gold(I) compound contains two thiosulfate ions that are bonded to gold. These ions may also undergo sensitization reactions in addition to the gold in a photographic silver halide emulsion. Therefore, this gold(I) compound is not appropriate in silver halide compositions in which an amount of sulfur less than a 2:1 molar ratio with gold is desired for chemical sensitization, and not appropriate in silver halide compositions in which sulfur or selenium sensitizers other than thiosulfate are desired, such as a silver halide composition containing thioureas as described in U.S. Pat. No. 4,810,626 of Burgmaier et al.

Gold(I) compounds are known that do not contain thiosulfate ligands or other ligands possessing labile sulfur. However, many such gold(I) compounds are not useful as chemical sensitizers for photographic silver halide materials because their dissociation constants are too high and provide low stability. Such gold(I) compounds are susceptible to disproportionation or reduction by gelatin components, especially those in photographic silver halide emulsions. Many gold(I) compounds are not sufficiently soluble to be easily dispersed in a photographic silver halide composition in a uniform and controllable manner.

One gold(I) compound that has been proposed is a gold(I) thiolate as described in U.S. Pat. No. 3,503,749 of Tavernier et al. This compound contains a sulfonic acid sodium salt substituent on the thiolate ligand to impart water solubility. However, the process for preparing such gold(I) compounds involves use of gold fulminate that is explosive and thus not desirable for practical use.

Other gold(I) compounds, such as those containing alkyl or aryl thiolate ligands are also not useful because the alkyl or aryl thiolate may be readily displaced from the gold compound by protons, as described in, for example, G. E. Coates, B. Kowala and J. M. Swan; *Aust. J. Chem.*, 19, 539 (1966).

Thus, there has been continuing interest in synthesizing new gold(I) compounds which have good stability and solubility properties and which contain ligands that will not undergo further reaction after dissociating from the gold(I) ion or interfere with the emulsion in any adverse way.

A well-known phenomenon in coordination chemistry that enhances the stability of metal ion complexes is the chelate effect (J. E. Huheey, "Inorganic Chemistry" 2nd ed., Harper & Row, New York, 1978, pp. 481–482). A chelate is a ligand that provides two or more coordination sites for a metal ion. A bidentate ligand, for example, will provide a lower dissociation constant (greater stability) for the complex ion than two separate monodentate ligands of the same type. Should one donor group of the bidentate temporarily dissociate, the second donor group will hold the ligand molecule in place so that it does not drift away, thereby favoring recombination.

Most bidentate ligands coordinate to metal ions in a cis configuration. But gold(I) normally requires linear, twofold coordination. Few bidentate ligands can extend for the trans coordination required by gold(I). Consequently, bidentate ligands generally form polymeric chains with gold(I) and mononuclear gold(I) chelates are quite rare. Even if there is a long separation between the two donor groups of a bidentate ligand that could accommodate the 180° C. coordination of gold(I), it is most probable that highly fluxional ligands will still form polymeric chains. These polymeric materials are not desirable because they tend to be insoluble and they also can have variable stoichiometry due to variable chain lengths. To increase the probability of forming a mononuclear chelate, the ligand molecule must be rigid, or at least have limited degrees of freedom, so that the two coordination sites are pointing at each other in close proximity. This situation could be provided by macrocyclic ligands and, in particular, macrocyclic thioether or selenoether compounds containing at least two sulfur and/or selenium atoms in the ring.

DISCLOSURE OF INVENTION

It is an object of this invention to provide gold(I) complexes comprising sulfur- and selenium-substituted macrocyclic polyether ligands, photographic elements containing the compounds, and emulsions containing the compounds. The compounds include monomers and dimers having the following formulas, respectively:

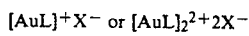

$[AuL]^+ X^-$ or $[AuL]_2^{2+} 2X^-$ wherein $X^-$ is any suitable anion such as tetrafluoroborate, nitrate, etc., and wherein L is a macrocyclic ligand containing at least two thioether and/or selenoether linkages and comprising from about 12 to about 30 members in the ring. The general structural formula for the macrocyclic compounds L may be represented as follows:

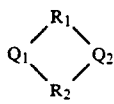

wherein $Q_1$ and $Q_2$ are each independently sulfur or selenium, and $R_1$ and $R_2$ are alkylene groups, the chain of which comprises from about 5 to 14 members that may include heteroatoms such as oxygen, sulfur, selenium, nitrogen, and that may include functional groups such as carboxylic ester or carboxylic amide linkages and the like. The alkylene group may be further substituted with alkyl groups or other functional groups such as carboxylic acids or esters, alcohols, and the like.

Examples of preferred novel gold compounds of the present invention are given in the following table:

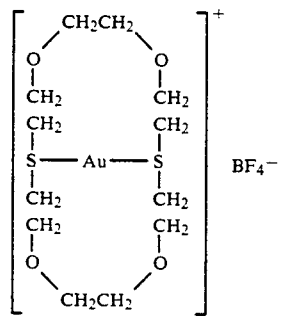

(1)

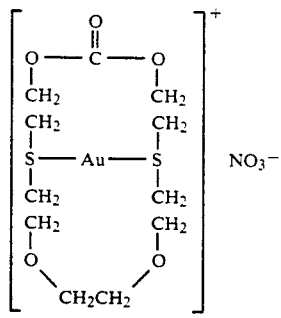

(2)

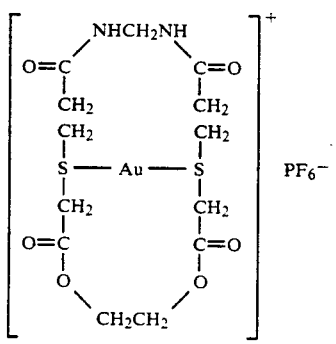

(3)

-continued

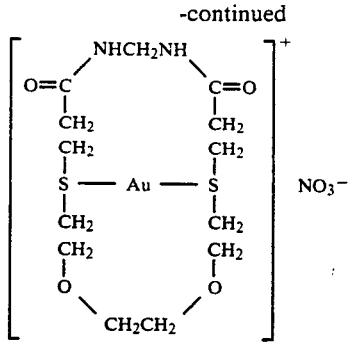

(4)

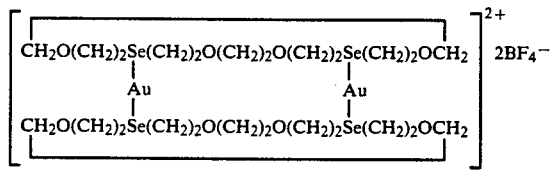

(5)

MODES FOR CARRYING OUT THE INVENTION

These invention types of gold(I) compounds have not previously been known as chemical sensitizers. Further, it is believed that they have not been known in the field of inorganic chemistry. The synthesis of the compounds was not expected since other known gold(I) compounds with ligands that contain two thioether linkages form two independent S-Au-Cl moieties which are not chelates and which are not useful for chemical sensitization because of their insolubility in suitable solvents [M. G. B. Drew and M. J. Riedl, J. Chem. Soc., Dalton Trans., p. 52 (1073)]. The selenium-containing compounds represent a further new class of compounds, as none have been previously described which contain gold(I) coordinated to a selenium atom of a selenoether functional group. The invention also provides photographic silver halide emulsions chemically sensitized with said compounds. That these compounds would, in fact, be active sensitizers is surprising since the gold(I) ions are enclosed by the macrocyclic ligands.

The compounds of the present invention comprising macrocyclic thioether or selenoether complexes of gold(I) are advantageous over acyclic thioether or selenoether complexes of gold(I) due to their enhanced stability that derives from the chelate effect. This enhanced stability is evidenced from the fact that the novel compounds may be synthesized by reactions in which the macrocyclic thioether will readily displace monodentate thioether ligands from a gold(I) precursor compound.

The novel gold(I) compounds of the present invention may exist as either monomers having the general formula $AuL^+X^-$, or dimers having the general formula $[Au_2L_2]^{2+}2X^-$. Of the specific examples above, compounds 1-4 are monomers, while compound 5 is a dimer.

A compound will have the same proportions of the constituent elements whether it exists as a monomer or dimer. Monomers and dimers may be distinguished by single-crystal x-ray diffraction methods, such as those described in G. H. Stout and L. H. Jensen, "X-Ray Structure Determination", Macmillan, New York, 1968.

It is theorized that during the course of the chemical sensitization reactions, complex ions containing gold(I) dissociate to release the gold to form the sensitivity centers on the silver halide grains. The ligands which had been coordinated to gold(I) in the complex ion are thus also released into the silver halide photographic emulsions. Because of the fact that compounds that function as ligands for gold(I) will usually also function as ligands for silver(I), there is continuing interest in finding gold(I) complexes which contain ligands that will not have adverse effects on the emulsion grains through the silver complexing activity.

There are many types of silver ligands which function variously as ripening agents, fixing agents, and development accelerators. The macrocyclic compounds used to form the gold(I) complex ions of the present invention have also been disclosed as ripening agents for silver halide photographic emulsions. In the practice of making an emulsion when these macrocyclic compounds are employed as grain growth modifiers, there is usually a step after the precipitation is complete in which most of the grain growth modifier is removed by a wash procedure. However, there is always some residual amount of these grain growth modifiers in the emulsion. Subsequent use of the sensitizer compounds of the present invention does not introduce any additional effect due to the release of the macrocyclic compounds into the emulsions since that macrocyclic thioether or selenoether compound, or a closely related compound, will already be present in the emulsion in amounts generally larger than that added as part of the gold sensitizer compound. However, if other gold(I) compounds containing different types of ligands were added, the ligands released from these compounds could lead to some disadvantageous effect such as poor storage keeping of the raw or coated emulsion, displacement of dye from the grains or development effects. Thus, the compounds of the present invention are the sensitizers of choice for use in emulsions which already contain thioether or selenoether grain growth modifiers. The use of the compounds of the present invention is, of course, not limited to these cases.

The macrocyclic compounds L used to form the novel gold(I) compounds may be synthesized by methods described by Dann and Gates, U.S. Pat. No. 3,062,646 and by Herz and Klaus, U.S. Pat. No. 4,782,013. Synthesis of the novel gold(I) compounds can be effected by various techniques. One convenient method comprises reacting a gold(I) precursor compound with an appropriate amount of the macrocyclic compound in a suitable solvent such as acetone at ambient temperature or slightly above. A suitable gold(I) precursor compound may be, for example, a gold(I) compound comprising two monodentate thioether ligands of the type described by Hill, U.S. Pat. No. 4,165,380. The product may then be isolated and purified by crystallization techniques.

This invention also provides a process for sensitizing a silver halide emulsion formed according to processes generally well-known in the art. A double jet-type process is preferred. The silver halide grains can comprise mixed or single halide components and especially include chloride, bromide, iodide, iodochloride, iodobromide or chlorobromide grains.

The double-jet process comprises adding an aqueous silver nitrate solution and an aqueous solution of one or more halides, for example, an alkali metal halide such as potassium bromide, potassium chloride, potassium iodide or mixtures thereof, simultaneously to a stirred solution of a silver halide protective colloid through two separate jets.

In the present invention, the described sensitizing gold(I) compounds may be added to a silver halide emulsion at various stages during its preparation. For example, the compounds may be added at levels from about $10^{-7}$ to about $10^{-3}$ mol thereof per mol of silver halide. A preferred concentration of gold compound to achieve sensitization of silver halide is from about $10^{-6}$ to about $10^{-4}$ mol thereof per mol of silver halide.

The gold(I) sensitizing compounds may be added singly or in combination with other sensitizing agents. They may also be added to a silver halide emulsion along with silver ion ligands and silver halide growth modifiers or stabilizers and antifogging agents, or with spectral or chemical sensitizing agents such as sulfur or selenium compounds or with dopants such as iridium complexes, during formation of silver halide grains, during the physical or chemical ripening stage, or in a separate step before coating.

Conditions for sensitizing silver halide grains such as pH, pAg, temperature, etc., are not particularly limited when employed using compounds described herein. The pH is generally about 1 to 9, preferably about 3 to 6, and pAg is generally about 5 to about 12, preferably from about 7 to about 10. Silver halide grains may be sensitized at temperatures between about 30° to about 90° C., with about 40° to about 70° C. being preferred.

Gelatin is preferred as the binder or protective colloid for the photographic emulsion of the present invention. However, other hydrophilic colloids are also suitable. For example, proteins such as gelatin derivatives, graft polymers of gelatin and other polymers, albumin, casein, cellulose derivatives such as hydroxyethyl cellulose, carboxymethyl cellulose and cellulose sulfate, sugar derivatives such as sodium alginate, starch derivatives and various synthetic peptizers such as hydrophilic homopolymers or copolymers such as polyvinyl alcohol, poly-N-vinylpyrrolidone, polyacrylic acid, polymethacrylic acid, polyacrylamide, polyvinylimidazole and polyvinyl pyrazole can be used.

Acid-processed gelatin can be used, as well as lime-processed gelatin. Further, gelatin hydrolyzates and enzyme-hydrolyzed products of gelatin are also usable.

Surface-active agents may be incorporated in a photographic emulsion layer or in another hydrophilic colloid layer as a coating aid to prevent buildup of static charge, to improve lubrication properties, to improve emulsion dispersion, to prevent adhesion and to improve other properties.

A photosensitive material of the present invention may contain antifogging agents or emulsion-stabilizing agents such as, for example, azaindenes, thionamides, azoles and the like.

The photographic silver halide emulsions as described can be used in photographic silver halide elements in any of the ways and for purposes known in the photographic art.

The photographic silver halide emulsions can be used and incorporated in photographic elements that are single color elements or multicolor elements. Multicolor elements contain dye image-forming units sensitive to each of the three primary regions of the visible spectrum. Each unit can be comprised of a single emulsion layer or of multiple emulsion layers sensitive to a given region of the spectrum. The layers of the element can be arranged in various orders as known in the art.

In the following discussion of suitable materials for use in emulsions and elements of the invention, reference will be made to *Research Disclosure*, December 1989, Item No. 308119. *Research Disclosure* is published by Kenneth Masons Publications Ltd., Dudley Annex, 12a North Street, Emsworth, Hampshire PO 10 7DQ, England. This publication will be identified hereafter by the term "Research Disclosure".

The silver halide emulsions of the invention can be used in elements that can be either negative-working or positive-working. The emulsions in which the described new chemical sensitizers can be used are described in, for example, *Research Disclosure* Sections I, II and III and the publications and patents cited therein. Useful vehicles for the emulsion layers and other layers of elements of the invention are described in *Research Disclosure* Section IX and the publications cited therein.

The described photographic emulsions can be used in color photographic elements with couplers as described in *Research Disclosure* Section VII and the publications cited therein. The couplers can be incorporated in the elements and emulsions as described in *Research Disclosure* Section VII and ways known in the art.

The photographic elements and emulsions as described can contain addenda known to be useful in photographic elements and emulsions in the photographic art. The photographic elements and emulsions as described can contain, for example, brighteners (see *Research Disclosure* Section V); antifoggants and stabilizers (see *Research Disclosure* Section VI); antistain agents and image dye stabilizers (see *Research Disclosure* Section VII); light absorbing and scattering materials (see *Research Disclosure* Section VIII); hardeners (see *Research Disclosure* Section X); coating aids (see *Research Disclosure* Section XI); plasticizers and lubricants (see *Research Disclosure* Section XII); antistatic agents (see *Research Disclosure* Section XIII); matting agents (see *Research Disclosure* Section XVI); and development modifiers (see *Research Disclosure* Section XXI).

The photographic silver halide materials and elements as described can be coated on a variety of supports as described in *Research Disclosure* Section XVII and the publications cited therein.

The photographic silver halide materials and elements as described can include coarse, regular and fine grain silver halide crystals or mixtures thereof and can be comprised of any photographic silver halides known in the photographic art.

The photographic silver halide materials as described can be spectrally sensitized by means and dyes known in the photographic art, such as by means of spectral sensitizing dyes as described in, for example, *Research Disclosure* Section IV and the publications cited therein. Combinations of spectral sensitizing dyes are especially useful.

Photographic materials and elements as described can be exposed to actinic radiation, typically in the visible region of the spectrum, to form a latent image as described in *Research Disclosure* Section XVIII and then processed to form a visible image as described in, for example, *Research Disclosure* Section XIX using developing agents and other processing agents known in the photographic art. Processing to form a visible image, typically a dye image, includes the step of contacting the element with a developing agent, typically a color developing agent, to reduce developable silver halide and oxidize the developing agent. In a color material the oxidized color developing agent in turn reacts with couplers to yield a dye.

The photographic silver halide materials can also be used in physical development systems as described in *Research Disclosure* Section XXII, in image-transfer systems as described in *Research Disclosure* Section XXIII, in dry development systems as described in *Research Disclosure* Section XXIV and in printing and lithography materials as described in *Research Disclosure* Section XXV.

The photosensitive materials obtained by the present invention can be processed according to known methods. A developer to be used for the black-and-white processing can contain conventional developing agents such as dihydroxybenzenes (e.g., hydroquinone), 3-pyrazolidones (e.g., 1-phenyl-3-pyrazolidone), aminophenols (e.g., N-methyl-p-amino-phenol), 1-phenyl-3-pyrazolidones or ascorbic acids.

As color-developing agent, there can be used primary aromatic amine developing agents such as phenylenediamines (e.g., 4-amino-N,N-diethylaniline, 3-methyl-4-amino-N,N-diethylaniline, 4-amino-3-methyl-N-hydroxyethylaniline, 3-methyl-4-amino-N-ethyl-N-hydroxyethylaniline, 3-methyl-4-amino-N-ethyl-N-methanesulfonamido-ethylaniline and 4-amino-3-methyl-N-ethyl-N-methoxyethylaniline. In addition, the developing agents described in L. F. A. Mason, *Photographic Processing Chemistry* (Focal Press, 1966), pp. 226–229, as well as those described in U.S. Pat. Nos. 2,193,015 and 2,592,364 may be used.

A photographic emulsion useful in the present invention can be applied to many different silver halide photographic light-sensitive materials due to its high photographic sensitivity, contrast, and fog reduction. For example, it can be used in high speed black-and-white negative films, in X-ray films and in multilayer color negative films.

The following examples further illustrate the invention. Parts and percentages are by weight unless otherwise indicated.

Synthesis of Compound 1

1,10-dithia-4,7,13,16-tetraoxacyclooctadecane (0.215 g) was dissolved in 8 mL ethanol at 50° C. This solution was added dropwise to a room temperature solution of bis(pentamethylenesulfide) gold(I) tetrafluoroborate (0.355 g prepared according to the method of Hill, U.S. Pat. No. 4,165,380) in 4 mL 1:1 acetone/ethanol. After stirring 15 min., a fine white precipitate began to appear. The solution was concentrated by evaporation, and then the white precipitate (0.384 g) was filtered and dried. The product could be recrystallized from hot acetone. The elemental analysis was consistent with the formula $AuS_2O_4C_{12}H_{24}BF_4$. A single-crystal x-ray diffraction study revealed that the gold atom is coordinated within the cavity of the macrocyclic ring by two sulfur atoms as represented by the structural formula given earlier. The molecule possesses a center of symmetry and the two Au-S bond lengths are 2.285(1)Å. The S-Au-S bond angle is exactly linear, as required by the crystallographic symmetry.

Synthesis of Compound 5

1,10-diselena-4,7,13,16-tetraoxacyclooctadecane (0.197 g) was dissolved in ethanol at about 50° C. and added dropwise to a solution of bis(pentamethylenesulfide) gold(I) tetrafluoroborate (0.247 g) dissolved in 5 mL acetone. Some precipitate formed after stirring about 45 min. at room temperature. The solvent was evaporated. After triturating the residue with ether, a white powder (0.293 g) was collected. The product could be recrystallized from hot acetone. Elemental analysis was consistent with the formula $AuSe_2C_{12}H_{24}O_4BF_4$, but a single-crystal x-ray diffraction study revealed that the compound is, in fact, a dimer with two gold atoms sandwiched between two of the crown selenaether rings as illustrated in the structural representation given earlier. The Au-Se bond lengths average 2.409Å. The Se-Au-Se bond angles of 174° C. deviate slightly from linearity.

EXAMPLES 1–3

Silver bromoiodide emulsions (3.5 mole % iodide) having predominantly cubic morphology with edge length measuring on average 0.37 micrometer were treated as follows: The emulsions were melted at 40° C. and the sensitizers listed in the table below were added. The temperature was raised to 65° C. and held for 15 min. After cooling the emulsions to 40° C., they were coated on film support at 300 mg Ag and 600 mg gelatin per ft². The dried coatings were exposed sensitometrically for 0.1 sec to a mercury lamp and then processed for 6 min. in KODAK Rapid X-Ray Developer. The log of the exposure required to produce an optical density of 0.2 above the minimum density (fog) was determined relative to that required for the unsensitized emulsion.

TABLE 1

| | Sensitizing Agent (mg/mol Ag) | Log Relative Speed (Fog) |
|---|---|---|
| 1 (control) | None | 0 (0.03) |
| 2 (control) | Compound S (2.2) | 1.25 (0.14) |
| 3 (invention) | Compound S (2.2), Compound 1 (4.6) | 2.19 (0.10) |

Compound S is a sulfur sensitizer (1,3-dicarboxymethyl-1,3-dimethyl-2-thiourea, disodium salt) of the type disclosed in Burgmaier and Herz, U.S. Pat. No. 4,810,626. When compound S is used alone as a sensitizer (comparison), a large increase in photographic speed is obtained relative to the unsensitized emulsion (control). The data in the table shows that use of compound 1 of the present invention in combination with compound S produces an additional large increase in the photographic speed while, at the same time, reduces the minimum density relative to use of compound S alone. This behavior of increasing speed and reducing minimum density (fog) relative to treatment with only a sulfur sensitizer shows that compound 1 is an effective gold sensitizing agent.

EXAMPLES 4–6

Silver chloride emulsions containing cubic grains with an average edge length of 0.63 micron, which were made in the presence of thioether silver halide ripeners of the type described in McBride U.S. Pat. No. 3,271,157 and containing 40 g gelatin per Ag mole were chemically and spectrally sensitized in the following manner:

The chemical sensitizers listed in Table 2 were added to the emulsion samples at 40° C. Then the temperature was raised to 60° C. and held 20 min. 250 mg/Ag mole of a blue spectral sensitizing dye having structure S-1 was added. The emulsion samples were then doctored with 92 mg/mole Ag of the antifoggant 1-(3-acetamidophenyl)-5-mercaptotetrazole sodium salt and 218 mg KBr/mole Ag. The emulsions were coated on paper support at 26 mg Ag/ft² and 144 mg gel/ft² with 100 mg per mole Ag of a yellow color-forming coupler having the structure S-2. An overcoat containing 100 mg gel/ft² was applied with a hardener.

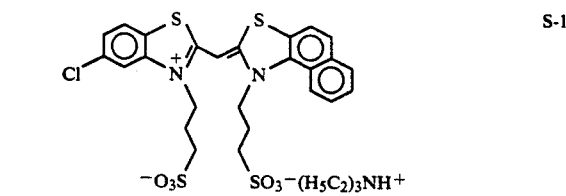

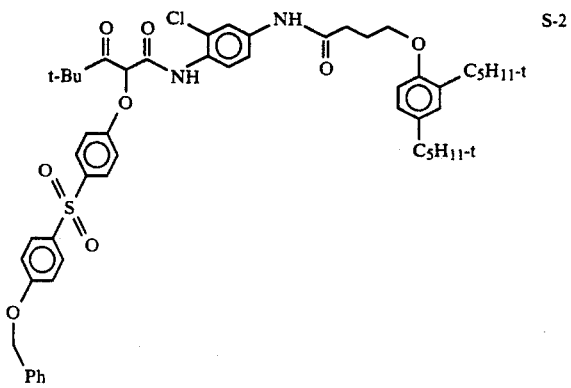

The dried coatings were exposed sensitometrically to a 3,000K tungsten source for 0.1 sec. through a step tablet ranging in optical density from 0 to 4 units. Processing was done through a standard Kodak RA4 process. The logarithms of the relative speeds were determined at a density of 1.0 above fog. The sensitometric responses are given below in Table II.

TABLE 2

| | Sensitizer | Log Relative Speed | Contrast |
|---|---|---|---|
| 4 (control) | 0.63 mg $Na_3Au(S_2O_3)_2.2H_2O$ | 158 | 193 |
| 5 (invention) | 0.30 mg $Na_2S_2O_3.5H_2O$, 0.69 mg compound 1 | 158 | 198 |
| 6 (invention) | 0.30 mg $Na_2S_2O_3.5H_2O$, 0.80 mg compound 5 | 162 | 199 |

It is seen from the data that a compound of the present invention used in combination with one molar equivalent of sulfur sensitizer results in a higher contrast compared to sensitization with an amount of aurous dithiosulfate equimolar in gold, which inherently contains two equivalents of the sulfur sensitizer thiosulfate.

The invention has been described in detail with particular reference to preferred embodiments thereof, but it will be understood that variations and modifications can be effected within the spirit and scope of the invention.

I claim:

1. A photographic silver halide emulsion chemically sensitized with a gold(I) compound having the formula:

$$[AuL]^+X^- \text{ or } [AuL]_2^{2+}2X^-$$

wherein L is a macrocyclic compound containing at least two thioether and/or selenoether groups within the ring and which comprises from about 12 to about 30 atoms in the ring structure, and wherein $X^-$ is an anion.

2. A photographic silver halide emulsion as in claim 1 wherein L is represented by the formula:

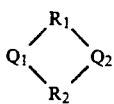

wherein $Q_1$ and $Q_2$ are each independently sulfur or selenium, and $R_1$ and $R_2$ are each alkylene groups, the chain of which each independently comprises from about 5 to 14 members that, in addition to carbon atoms, may include heteroatoms such as oxygen, sulfur, selenium, nitrogen, and that may include functional groups such as carboxylic ester or carboxylic amide linkages and the like. The alkylene groups may be further substituted with alkyl groups or other functional groups such as carboxylic acids or esters, amides, alkoxides, alcohols, and the like.

3. A photographic silver halide as in claim 1 wherein L is represented by the formula:

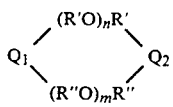

wherein $Q_1$ and $Q_2$ are each independently sulfur or selenium, R' and R" are each alkylene groups containing from 2 to about 4 carbon atoms, and n and m are each integers from 1 to about 3.

4. A photographic silver halide emulsion as in claim 1 wherein the gold compound has the formula:

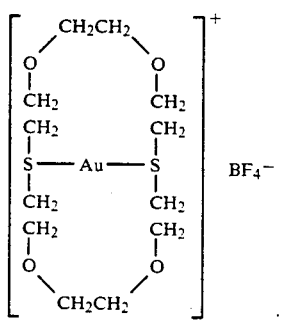

5. A photographic silver halide emulsion as in claim 1 wherein the gold compound has the following formula:

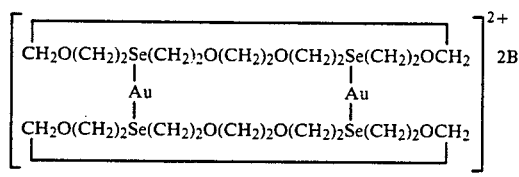

6. A photographic silver halide emulsion as in claim 1 which is a silver bromide, silver chloride, silver bromoiodide, silver chlorobromide, silver chloroiodide, or silver bromochloroiodide emulsion.

7. A photographic silver halide emulsion as in claim 1 also comprising a chemical sensitizing concentration of at least one added gold, sulfur, selenium, or reduction sensitizer.

8. A photographic silver halide emulsion as in claim 1 also comprising at least one sulfur chemical sensitizer comprising 1,3-dicarboxymethyl-1,3-dimethyl-2-thiourea, disodium salt.

9. A photographic silver halide element comprising a support bearing at least one photographic silver halide emulsion layer comprising a photographic silver halide emulsion chemically sensitized with a gold(I) compound having the formula:

$$[AuL]^+X^- \text{ or } [AuL]_2^{2+}2X^-$$

wherein L is a macrocyclic compound containing at least two thioether and/or selenoether groups within the ring and which comprises from about 12 to about 30 atoms in the ring structure, and wherein $X^-$ is an anion.

10. The photographic silver halide element of claim 9 wherein a color photographic silver halide element and said silver halide comprises silver bromoiodide.

11. The photographic silver halide element of claim 9 wherein said silver halide comprises at least one of silver bromide, silver chloride, silver chlorobromide, or silver chlorobromoiodide 12. The photographic silver halide element as in claim 9 wherein L is represented by the formula:

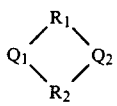

wherein $Q_1$ and $Q_2$ are each independently sulfur or selenium, and $R_1$ and $R_2$ are each alkylene groups, the chain of which each independently comprises from about 5 to 14 members that, in addition to carbon atoms, may include heteroatoms such as oxygen, sulfur, selenium, nitrogen, and that may include functional groups such as carboxylic ester or carboxylic amide linkages and the like. The alkylene groups may be further substituted with alkyl groups or other functional groups such as carboxylic acids or esters, amides, alkoxides, alcohols, and the like.

13. The photographic silver halide element of claim 9 further comprising a chemical sensitizing concentration of at least one added gold, sulfur, selenium, or reduction sensitizer.

14. The photographic silver halide emulsion of claim 9 further comprising at least one sulfur chemical sensitizer comprising 1,3-dicarboxymethyl-1,3-dimethyl-2-thiourea, disodium salt.

15. The photographic silver halide element of claim 12 wherein L is represented by the formula:

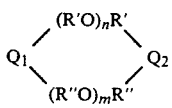

wherein $Q_1$ and $Q_2$ are each independently sulfur or selenium, R' and R" are each alkylene groups containing from 2 to about 4 carbon atoms, and n and m are each integers from 1 to about 3.

16. The photographic silver halide emulsion of claim 12 wherein the gold compound has the formula:

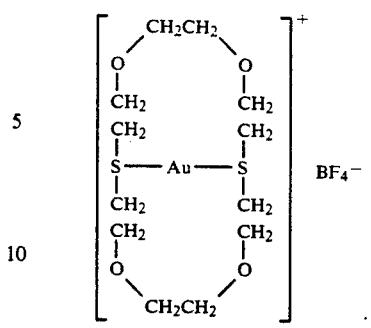
17. The photographic silver halide emulsion of claim 12 wherein the gold compound has the following formula:
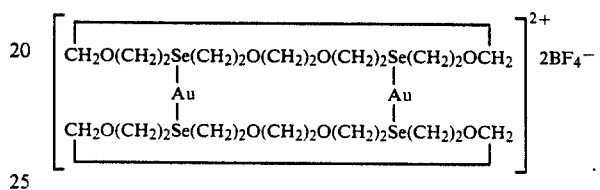
* * * * *